United States Patent
Montasser et al.

(10) Patent No.: US 7,348,031 B2
(45) Date of Patent: Mar. 25, 2008

(54) METHOD FOR PREPARING COLLOIDAL PARTICLES IN THE FORM OF NANOCAPSULES

(75) Inventors: Imed Montasser, Villeurbanne (FR); Hatem Fessi, Lyons (FR); Stephanie Briancon, Villeurbanne (FR); Joseph Lieto, Genas (FR)

(73) Assignee: Universite Claude Bernard Lyon I, Villeurbanne Cedex (FR)

( * ) Notice: Subject to any disclaimer, the term of this patent is extended or adjusted under 35 U.S.C. 154(b) by 548 days.

(21) Appl. No.: 10/203,656

(22) PCT Filed: Mar. 2, 2001

(86) PCT No.: PCT/FR01/00623

§ 371 (c)(1),
(2), (4) Date: Oct. 18, 2002

(87) PCT Pub. No.: WO01/68235

PCT Pub. Date: Sep. 20, 2001

(65) Prior Publication Data

US 2003/0059473 A1 Mar. 27, 2003

(30) Foreign Application Priority Data

Mar. 10, 2000 (FR) .................................. 00 03133

(51) Int. Cl.
*A61K 9/50* (2006.01)
(52) U.S. Cl. ..................... 424/501; 424/489; 424/400
(58) Field of Classification Search .................. 264/4.6, 264/4.1
See application file for complete search history.

(56) References Cited

U.S. PATENT DOCUMENTS

| | | | | |
|---|---|---|---|---|
| 4,487,759 A | * | 12/1984 | Nesbitt et al. ............... | 424/497 |
| 5,049,322 A | * | 9/1991 | Devissaguet et al. ......... | 264/4.1 |
| 5,174,930 A | * | 12/1992 | Stainmesse et al. ......... | 264/4.6 |
| 5,500,224 A | | 3/1996 | Vranckx | |
| 5,783,211 A | * | 7/1998 | Manzo et al. ............... | 424/450 |

FOREIGN PATENT DOCUMENTS

| | | |
|---|---|---|
| FR | 2766368 | 7/1997 |
| JP | 06-170214 | 6/1994 |
| JP | 07-116500 | 5/1995 |
| WO | 94/13139 | 6/1994 |
| WO | 94/15590 | 7/1994 |

* cited by examiner

OTHER PUBLICATIONS

Derwent Acc No. 1986-335063 Apr. 28, 1986.*

*Primary Examiner*—Michael P. Woodward
*Assistant Examiner*—Eric E. Silverman
(74) *Attorney, Agent, or Firm*—Dennison, Schultz & MacDonald

(57) ABSTRACT

The invention relates to a process for the preparation of dispersible colloidal systems in the form of nanocapsules whose wall consists of a polymer obtained by the polycondensation of two monomers, α and β, and whose core consists of a substance B, characterized in that:

(1) a first liquid phase is prepared which consists of a solution of monomer α in a solvent or solvent mixture and contains one or more surfactants and the substance B in solution or suspension;
(2) a second liquid phase is prepared which consists of a non-solvent or non-solvent mixture for the monomer α and contains the monomer β and one or more surfactants, the solvent or solvent mixture of the first phase being miscible in all proportions with the non-solvent or non-solvent mixture of the second phase;
(3) the first phase is added to the second, with moderate agitation, to give a colloidal suspension of nanocapsules, agitation being maintained until the monomers α and β have completely polymerized; and
(4) if desired, all or part of the solvent or solvent mixture and non-solvent or non-solvent mixture is removed to give a colloidal suspension having the desired concentration of nanocapsules.

20 Claims, 1 Drawing Sheet

INFLUENCE OF THE AMOUNT OF TEREPHTHALOYL CHLORIDE ON THE SIZE OF THE NANOCAPSULES

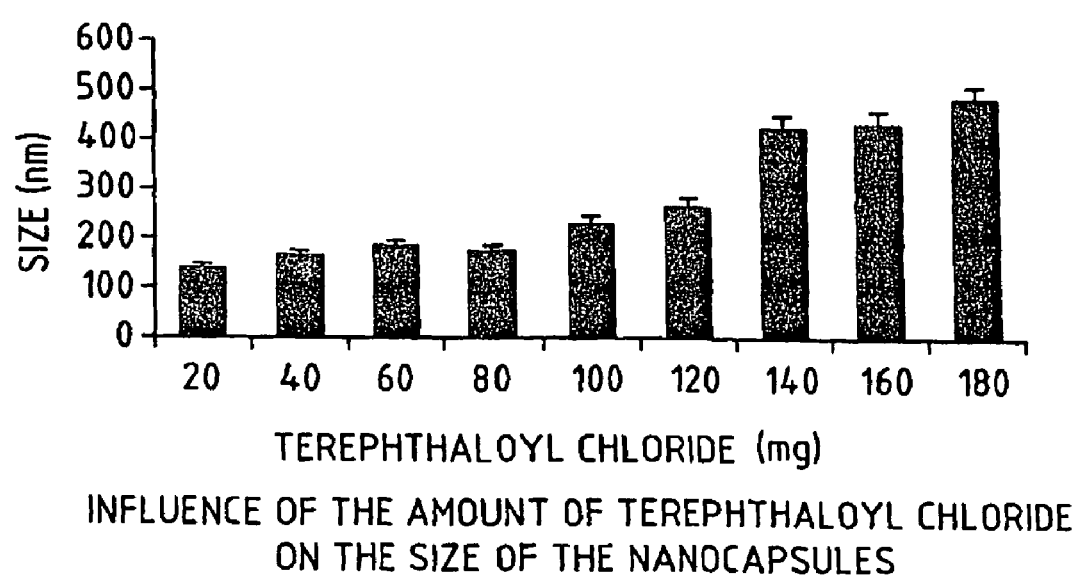
INFLUENCE OF THE AMOUNT OF TEREPHTHALOYL CHLORIDE
ON THE SIZE OF THE NANOCAPSULES
FIGURE

METHOD FOR PREPARING COLLOIDAL PARTICLES IN THE FORM OF NANOCAPSULES

This application is a filing under 35 USC 371 of PCT/ FR01/00623 filed Mar. 2, 2001.

The invention relates to a novel process for the preparation of colloidal particles in the form of nanocapsules by interfacial polycondensation.

The vectorization of active principles is a technique which has undergone considerable and rapid development and has formed the subject of numerous researches in recent years, culminating in the design of various forms of colloidal particles in which an active molecule is associated with a carrier. In fact, the use of drug vectors has the advantage of being able to influence the process of distribution of the active principle in the organism and of increasing its efficacy. The active molecule incorporated in a carrier material can be specifically directed towards the target to be treated, where its concentration is then locally high. This enhances the efficacy while at the same time reducing the doses required and hence also the risks of side effects due to the pervasion of other organs.

The association of the carrier material with the active principle can be effected in various ways, depending on the type of particles and the desired effect. The active molecule can be dissolved, dispersed or encapsulated in the particle, or it can be adsorbed or fixed on the surface of the particle. In the first case, the active principle will be released by dissolution of the polymer constituting the particle or its membrane, or by diffusion through the latter. The nature and structure of the polymer network, especially its porosity, thus play a fundamental role. In the case of surface binding, this must be reversible in order to release the principle at the target to be treated. It is also of interest to modify the nature of the polymer used so as to vary characteristics such as porosity, biodegradability, transfer properties and the bioavailability of the active principle.

The methods of preparing colloidal vectors are diverse, each of them allowing the use of specific reagents and giving rise to a given type of particle.

The methods involving solution polymerization utilize mainly two types of monomer: acrylic acid derivatives and alkyl cyanoacrylates. Patents BE-A-808 034 and BE-A-839 748 describe the formation of submicron particles by the micellar polymerization of an acrylic acid derivative, for example methyl or butyl methacrylate, or a mixture of several monomers, in order to prepare a methacrylic copolymer. The polymerization reaction takes place in the aqueous phase in the presence of a chemical free radical initiator at a temperature of about 90° C., with agitation. The initiation can also be effected e.g. by gamma irradiation. The particles obtained are spherical with a size of between 200 and 500 nm. They can be used as a drug vector by fixing various pharmacologically active molecules on their surface. Although their formulation is stable and reproducible, this stability constitutes one of the major disadvantages of this type of particle. In fact, the majority of acrylic polymers possess a very slow or even zero biodegradability, resulting in a possible accumulation of the material in the tissues.

Patent application EP 007 895 describes the formation of nanoparticles obtained by the polymerization of an alkyl cyanoacrylate and containing a biologically active substance. In this process the monomer is added to an aqueous phase containing a surfactant, with vigorous agitation. Anionic polymerization, initiated by the hydroxyl ions in the aqueous phase, takes place at room temperature. The pH of the solution controls the polymerization rate and has to be low (between 2 and 3) to optimize particle formation. The active principle is generally introduced during the polymerization in order to be incorporated into the particles, unless it is likely to be degraded by the acidity of the medium, in which case it has to be adsorbed on the surface after the particles have formed. Polymers based on alkyl cyanoacrylate are rapidly biodegradable, but their use can be limited by the appreciable toxicity of the degradation products.

Patent applications FR-A-2 504 408 and FR-A-2 515 960 disclose a method of forming nanocapsules based on alkyl cyanoacrylate in which the cyanoacrylic monomer is dissolved in a water-miscible solvent containing an oil. This solution is introduced into an aqueous phase, with agitation. Diffusion of the organic solvent takes place simultaneously with polymerization of the monomer at the oil/water interface. The nanocapsules have a mean diameter of between 200 and 300 nm and a very low wall thickness of a few nanometers, according to ALKHOURI et al., Pharm. Acta Helv., 61, 274-281, 1986.

The process according to the invention enables nanocapsules based on polymers associated in a novel manner in this application to be obtained by a technique involving the interfacial polycondensation of two monomers. According to an advantageous feature, said nanocapsules have a mean diameter of less than 600 nm, especially of between 50 and 600 nm.

The invention therefore relates to a process for the preparation of dispersible colloidal systems in the form of nanocapsules whose wall consists of a polymer obtained by the polycondensation of two monomers, $\alpha$ and $\beta$, and whose core consists of a substance $\beta$, characterized in that:

(1) a first liquid phase is prepared which consists of a solution of monomer an in a solvent or solvent mixture and contains at least one surfactant and the substance B in solution or suspension;

(2) a second liquid phase is prepared which consists of a non-solvent or non-solvent mixture for the monomer $\alpha$ and the substance B and contains the monomer $\beta$ and at least one surfactant, the solvent or solvent mixture of the first phase being miscible in all proportions with the non-solvent or non-solvent mixture of the second phase, and the concentration of the monomer $\beta$ being in at least a 5-fold excess, in terms of the number of moles, relative to the concentration of the monomer $\alpha$;

(3) the first phase is added to the second, with moderate agitation, to give a colloidal suspension of nanocapsules, agitation being maintained until the monomers $\alpha$ and $\beta$ have completely polymerized; and (4) if desired, all or part of the solvent or solvent mixture and non-solvent or non-solvent mixture is removed to give a colloidal suspension having the desired concentration of nanocapsules.

In step (4) it is also possible, if desired, to obtain a powder of nanocapsules by employing a technique of desiccation (nebulization, lyophilization) after the addition of stabilizing substances such as sugars, lactose, glucose, etc.

In contrast to the processes described above, the 2 monomers are introduced into the 2 phases right at the beginning, rather than successively after a stable nanoemulsion has been obtained in the first phase.

As the solvent or solvent mixture of the first phase is miscible in all proportions with the non-solvent or non-solvent mixture of the second phase, its diffusion into the second phase at the time of injection causes the instantaneous formation of oily droplets with a mean diameter of less than 300 nm. Simultaneously the monomer $\beta$ diffuses into the first phase and the polycondensation reaction takes place at the oil/water interface to form the nanocapsule membrane.

Drop formation and the start of polymerization occur simultaneously. The polymerization is not free but actually takes place at the oil/water interface, and the particles formed are of the capsule type. The novelty of the process according to the invention lies in the fact that the two monomers initially present in each of the phases react at the interface of the droplets as soon as the latter form, despite the small size of the dispersion. It is therefore unnecessary to use a process involving two successive phases comprising firstly the creation of the emulsion and then the addition of the second monomer to start the polymerization.

Compared with an emulsion polymerization, often demanding a lengthy methodology which is difficult to implement, the process according to the invention therefore has the advantage of great simplicity insofar as it does not require the presence of a polymerization initiator or a special device for creating the emulsion.

Particle formation is instantaneous, but the kinetics of the polymerization reaction depend on the chemical nature and the concentration of the two monomers in the 2 phases.

The solvent or solvent mixture of the first phase is advantageously an organic solvent or organic solvent mixture, so the first phase will constitute the organic phase and the non-solvent or non-solvent mixture of the second phase will constitute the aqueous phase.

According to another feature of the process according to the invention, it is also possible to use two organic phases or two aqueous phases provided the following conditions are satisfied: solubility of the monomer $\alpha$ in the solvent or solvent mixture of the first phase, insolubility of the monomer $\alpha$ in the non-solvent or non-solvent mixture of the second phase, miscibility of the solvent or solvent mixture of the first phase and the non-solvent or non-solvent mixture of the second phase, and their non-reactivity with the monomers.

Insofar as it does not react with the monomer $\alpha$, the solvent can be e.g. an organic, preferably volatile solvent selected from a lower ketone (acetone, methyl ethyl ketone, etc.), a light hydrocarbon or light hydrocarbon mixture (hexane, etc.), a chlorinated light hydrocarbon (chloroform, methylene chloride), other customary solvents (acetonitrile, dioxane, tetrahydrofuran, etc.) and mixtures thereof.

Provided the conditions of solubility, insolubility, miscibility and non-reactivity with the monomers are satisfied, the solvent or solvent mixture of the first phase can constitute from 10 to 90% of the final mixture, preferably from 20 to 60% of the final mixture and particularly preferably from 25 to 50%.

Insofar as it does not react with the monomer $\beta$ and is miscible in all proportions with the solvent or solvent mixture of the first phase, the non-solvent or non-solvent mixture can be e.g. water, an aqueous solution or any other solvent or organic liquid that satisfies the above-mentioned conditions.

Advantageously the concentration of the monomer $\alpha$ in the solvent or solvent mixture of the first phase is between 0.01 and 20% by weight, preferably between 0.1 and 10% and particularly preferably between 0.2 and 5%. The concentration of the monomer $\beta$ in the non-solvent or non-solvent mixture of the second phase can likewise be between 0.05 and 50% by weight, preferably between 0.5 and 40% and particularly preferably between 1 and 25%.

According to one preferred feature, the monomer $\alpha$ is selected from acid dichlorides and diisocyanates. Particularly preferred monomers $\alpha$ are terephthaloyl chloride, sebacoyl chloride, toluylene-2,4-diisocyanate and hexamethylene diisocyanate.

According to another preferred feature of the invention, the monomer $\beta$ is a diamine, for example diethylenetriamine, dimethylenediamine or hexamethylene-diamine, or a glycol derivative.

According to an advantageous feature, the concentration of the monomer $\beta$ is in excess, preferably in at least a 5-fold excess, in terms of the number of moles, relative to that of the monomer $\alpha$.

The sole drawing figure is a bar graph showing the influence of the amount of terephthaloyl chloride on the size of nanocapsules.

It has in fact been found, surprisingly, that the conditions discussed above confer a high stability on the nanocapsules and make it possible, by increasing the concentration of monomer $\alpha$, to increase the thickness of the nanocapsule membrane as desired, resulting in an increase in the mean diameter of the nanocapsules. As shown in the Figure, given that all the other proportions are maintained, this increase in the mean diameter can only be explained by an increase in the thickness of the nanocapsule membrane.

One hypothesis is that polymerization continues to take place at the nanocapsule membrane whereas, in the processes described in the prior art, polymerization stops after the formation of a first fine polymer membrane.

The process according to the invention therefore advantageously makes it possible, according to the monomers used and the thickness of the polymer membrane, to obtain nanocapsules of controlled biodegradability, or even, if desired, to obtain nanocapsules with an insoluble non-biodegradable membrane capable of constituting a reservoir of active principle which is released solely by diffusion through the polymer membrane.

The substance B can be any substance that is soluble or dispersible in the chosen solvent or solvent mixture. In particular, the substance B can be a vegetable or mineral oil or any oily substance, for example olive oil, benzyl benzoate, isopropyl myristate, a fatty acid glyceride or sweet-almond oil.

The substance B can also be a biologically active substance, for example a molecule which can be used as an active principle of a drug or as a precursor of an active principle of a drug, or else a contrast agent or a biological reagent.

The substance B can also be a pigment, an ink, a lubricant or a surface treatment agent.

A mixture of the above substances, for example an oil containing one or more of these substances in solution or suspension, can also be used as the substance B.

The surfactants used can be natural surfactants or synthetic ionic, non-ionic or amphoteric surfactants.

In each of the phases, the surfactant or surfactant mixture is present in an amount of 0.01 to 10% by weight, preferably of 0.1 to 1% by weight.

The ionic surfactant used will be e.g. sodium laurylsulfate.

The non-ionic surfactants used, depending on the phase in which they are present, will preferably be surfactants with a high hydrophilic/lipophilic balance (HLB), such as polyethoxylated sorbitan derivatives (of the Tween® type), ethylene oxide/propylene oxide copolymers (of the Pluronic® type) or ethers of fatty alcohols and polyoxyethylene glycol, or on the other hand surfactants with a low hydrophilic/lipophilic balance, such as sorbitan derivatives (of the Span® type).

The amphoteric surfactants used will be e.g. egg or soy lecithin or purified derivatives thereof.

According to a preferred feature of the process, the first phase is an organic phase and the surfactant used is one or more amphoteric and/or non-ionic surfactants selected from those mentioned above, preferably those with a low hydrophilic/lipophilic balance.

Advantageously the second phase is an aqueous phase in which the surfactant used is one or more ionic and/or non-ionic surfactants selected from those mentioned above, preferably those with a high hydrophilic/lipophilic balance.

The reaction takes place at room temperature, with moderate agitation. The polymerization time is variable and depends on the composition of each of the phases.

Agitation is not essential for the formation of the nanocapsules, but makes it possible to homogenize the preparation, especially when large volumes are used.

When the polymerization is complete, the solvent or solvent mixture and the non-solvent or non-solvent mixture in the final mixture can be at least partially removed by evaporation under reduced pressure, by an appropriate desiccation method or by tangential ultrafiltration, this technique also making it possible to remove any residual monomers.

The nanocapsules obtained have a mean diameter of between 50 and 600 nm and their population is monodisperse. They can be kept in an aqueous medium.

The process according to the invention can be adapted to various pairs of monomers in order to form different types of polymers according to the application envisaged, for example polyamide, polyurea, polyurethane, polyester, poly-carbonate, polysulfonate, polysulfonamnide, etc.

The wide choice of monomer pairs makes it possible to have nanocapsules of controlled biodegradability (controlled according to the thickness of the membrane and the nature of the chosen pair), which the prior art cannot offer.

Depending on the monomers, and in contrast to the prior art, it is possible to obtain an insoluble non-biodegradable membrane; this gives a reservoir of active product which is released solely by diffusion through the polymer membrane.

The choice of different types of polymers enables the particles formed to be used for a very wide variety of applications in numerous industrial fields, especially human and veterinary medicine, cosmetics, chemistry, agrochemistry, etc.

The invention is illustrated by the following Examples without implying a limitation:

EXAMPLE 1

Preparation of Polyamide Nanocapsules

An organic solution is prepared by dissolving 100 mg of terephthaloyl chloride, 200 mg of Miglyol® 812 oil (neutral oil formed of a mixture of $C_8$-$C_{10}$ fatty acid triglycerides) and 40 mg of lecithin (Lipoïd® S75) in 20 ml of acetone.

An aqueous phase is prepared by dissolving 500 mg of diethylenetriamine and 60 mg of Pluronic® F68 (mixed polymer of ethylene oxide and propylene glycol) in 40 ml of water. The organic phase is injected into the aqueous phase and the nanocapsules form instantaneously. Moderate magnetic agitation (500 rpm) is maintained until polycondensation has ended. Finally, the organic solvent and part of the water are removed by evaporation. The mean diameter of the nanocapsules, measured using a laser granulometer (COULTER® LS 230), is 300 nm.

EXAMPLE 2

The procedure of Example 1 is followed except that the diethylenetriamine is replaced with dimethylenediamine to give nanocapsules with a mean diameter of 285 nm.

EXAMPLE 3

The procedure of Example 1 is followed except that the 500 mg of diethylenetriamine are replaced with 500 mg of hexamethylenediamine to give nanocapsules with a mean diameter of 500 nm.

EXAMPLE 4

The procedure of Example 1 is followed except that the 100 mg of terephthaloyl chloride are replaced with 100 mg of sebacoyl chloride to give nanocapsules with a mean diameter of 300 nm.

EXAMPLE 5

The procedure of Example 1 is followed except that the amount of Miglyol® 812 is increased to 300 mg to give nanocapsules with a mean diameter of 415 nm.

EXAMPLE 6

The procedure of Example 1 is followed except that the amount of terephthaloyl chloride is increased to 140 mg to give nanocapsules with a mean diameter of 440 nm.

EXAMPLE 7

The procedure of Example 1 is followed except that 20 mg of Span® 80 are added to the acetone phase to give nanocapsules with a mean diameter of 280 nm.

EXAMPLE 8

The procedure of Example 1 is followed except that 30 mg of Tween® 80 are added to the aqueous phase to give nanocapsules with a mean diameter of 290 nm.

EXAMPLE 9

Preparation of Polyurea Nanocapsules

The procedure of Example 1 is followed except that the 100 mg of terephthaloyl chloride are replaced with 100 mg of toluylene-2,4-diisocyanate to give nanocapsules with a mean diameter of 120 nm.

EXAMPLE 10

The procedure of Example 1 is followed except that the 100 mg of terephthaloyl chloride are replaced with 100 mg of hexamethylene diisocyanate to give nanocapsules with a mean diameter of 118 nm.

EXAMPLE 11

Preparation of Polyamide Nanocapsules Containing Lidocaine

An organic solution is prepared by dissolving 100 mg of terephthaloyl chloride, a solution of 40 mg of lidocaine in 200 mg of oil (Miglyol® 812) and 40 mg of lecithin (Lipoïd® S75) in 20 ml of acetone.

An aqueous phase is prepared by dissolving 500 mg of diethylenetriamine and 60 mg of Pluronic® F68 in 40 ml of water.

The organic phase is injected into the aqueous phase and the nanocapsules form instantaneously.

Agitation is maintained until polycondensation has ended. Finally, the organic solvent and part of the water are removed by evaporation. The nanocapsules obtained have a mean diameter of 318 nm.

After standing for a prolonged period of several days, the bluish-white appearance of the suspension remains unchanged and, in particular, neither rupture of the nanocapsules nor a considerable variation in their size is observed.

EXAMPLE 12

Preparation of Polyamide Nanocapsules Containing Progesterone

The procedure of Example 9 is followed except that 5 mg of progesterone are added to the organic phase to give nanocapsules with a mean diameter of 148 nm. The suspension retains its appearance after storage for several days.

The invention claimed is:

1. A process for the preparation of dispersible colloidal systems in the form of nanocapsules of mean diameter less than 600 nm, and having a wall comprising a polymer obtained by the polycondensation of a monomer $\alpha$ and a monomer $\beta$, and a core comprising a substance B,
   wherein monomer $\alpha$ is selected from the group consisting of acid dichlorides and diisocyanates, monomer $\beta$ is selected from the group consisting of diamines, triamines and glycols, and substance B is an oil,
   comprising the steps of:
   (1) preparing a first liquid mixture comprising:
       a liquid solvent or solvent mixture for monomer $\alpha$;
       monomer $\alpha$ dissolved in the liquid solvent or solvent mixture;
       at least one surfactant in solution; and
       substance B in solution or suspension;
   (2) preparing a second liquid mixture comprising:
       a liquid non-solvent or non-solvent mixture for monomer $\alpha$ and the substance B;
       monomer $\beta$ dissolved in the liquid non-solvent or non-solvent mixture; and
       at least one surfactant in solution,
   wherein the solvent or solvent mixture is miscible in all proportions with the non-solvent or non-solvent mixture, and monomer $\beta$ is present in a concentration which is at least a 5-fold excess, in terms of the number of moles, relative to the concentration of the monomer $\alpha$;
   (3) adding the first mixture to the second mixture, with moderate agitation, to give a colloidal suspension of nanocapsules, and maintaining agitation until completion of polymerization; and
   (4) optionally, removing all or part of the solvent or solvent mixture and non-solvent or non-solvent mixture to give a colloidal suspension having the desired concentration of nanocapsules.

2. The process according to claim 1, wherein the solvent or solvent mixture of the first mixture is an organic solvent or organic solvent mixture and the non-solvent or non-solvent mixture of the second mixture constitutes an aqueous mixture.

3. The process according to claim 1, wherein the concentration of the monomer $\alpha$ in the solvent or solvent mixture of the first mixture is between 0.01 and 20% by weight.

4. The process according to claim 1, wherein the concentration of the monomer $\beta$ in the non-solvent or non-solvent mixture of the second mixture is between 0.05 and 50% by weight.

5. The process according to claim 1, wherein the substance B is at least one of a vegetable and mineral oil.

6. The process according to claim 1, wherein the substance B is a biologically active substance.

7. The process according to claim 1, wherein the substance B is an oil containing one or more biologically active substances in solution or suspension.

8. The process according to claim 1, wherein the surfactant or surfactant mixture is present in each liquid mixture in an amount of 0.01 to 10% by weight.

9. The process according to claim 1, wherein the first phase is an organic phase and the surfactant used is at least one amphoteric and/or non-ionic surfactant.

10. The process according to claim 1, wherein the second mixture is an aqueous phase and the surfactant used is at least one ionic and/or non-ionic surfactant.

11. The process according to claim 1, wherein the nanocapsules obtained have a mean diameter of between 50 and 600 nm.

12. The process according to claim 1, wherein the solvent or solvent mixture of the first mixture and, optionally, the non-solvent or non-solvent mixture of the second mixture are at least partially removed by evaporation, by desiccation or by tangential ultrafiltration.

13. The process according to claim 1, additionally comprising obtaining a powder of nanocapsules by addition of at least one stabilizing substance to the colloidal suspension and by application of a desiccation technique.

14. The process according to claim 4, wherein the concentration of the monomer $\beta$ in the non-solvent or non-solvent mixture of the second mixture is between 0.5 and 40% by weight.

15. The process according to claim 14, wherein the concentration of the monomer $\beta$ in the non-solvent or non-solvent mixture of the second mixture is between 1 and 25% by weight.

16. The process according to claim 8, wherein the surfactant or surfactant mixture is present in each liquid mixture in an amount of 0.1 to 1% by weight.

17. The process according to claim 3, wherein the concentration of the monomer $\alpha$ in the solvent or solvent mixture of the first mixture is between 0.1 and 10% by weight.

18. The process according to claim 3, wherein the concentration of the monomer $\alpha$ in the solvent or solvent mixture of the first mixture is between 0.1 and 10%.

19. The process according to claim 18, wherein the concentration of the monomer $\alpha$ in the solvent or solvent mixture of the first mixture is between 0.2 and 5%.

20. The process according to claim 2, wherein the solvent or solvent mixture of the first mixture is selected from the group consisting of acetone, methyl ethyl ketone, hexane, chloroform, methylene chloride, acetonitrile, dioxane, tetrahydrofuran, and mixtures thereof.

* * * * *